United States Patent [19]
Kallai-Sanfacon

[11] Patent Number: 4,492,706
[45] Date of Patent: Jan. 8, 1985

[54] METHOD OF LOWERING LIPID LEVELS

[75] Inventor: Mary-Ann Kallai-Sanfacon, Mount Royal, Canada

[73] Assignee: American Home Products Corporation, New York, N.Y.

[21] Appl. No.: 518,997

[22] Filed: Aug. 1, 1983

[51] Int. Cl.[3] ................. A61K 31/425; A61K 31/209; A61K 31/195

[52] U.S. Cl. .................................... 424/270; 424/316; 424/319

[58] Field of Search ......................... 424/319, 316, 270

[56] References Cited

U.S. PATENT DOCUMENTS 4,391,825 7/1983 Bellini et al. ........................ 424/319
4,439,617 3/1984 Sestanj et al. ....................... 424/309
4,446,150 5/1984 Sestanj et al. ....................... 424/270

FOREIGN PATENT DOCUMENTS 82300940.2 9/1982 European Pat. Off. .

*Primary Examiner*—Leonard Schenkman
*Assistant Examiner*—Joseph A. Lipovsky

[57] ABSTRACT

Disclosed herein is a method of lowering lipid levels in a mammal involving the administration of the following N-naphthoylglycine derivatives, or a therapeutically acceptable salt with an organic or inorganic base of the first three listed derivatives: N-[[5-(trifluoromethyl)-6-methoxy-1-naphthalenyl]-thioxomethyl]-N-methylglycine, N-[(5-bromo-1-naphthalenyl)thioxomethyl]-N-methylglycine, N-[[6-methoxy-5-(trifluoromethylthio)-1-naphthalenyl]thioxomethyl]-N-methylglycine, and 5-hydroxy-2-[5-(trifluoromethyl)-6-methoxy-1-naphthalenyl]-3-methylthiazolium hydroxide, inner salt.

9 Claims, No Drawings

METHOD OF LOWERING LIPID LEVELS

FIELD OF THE INVENTION

This invention relates to a method of lowering lipid levels in a mammal by administering thereto a N-napthoylglycine derivative selected from the group consisting of N-[[5-(trifluoromethyl)-6-methoxy-1-naphthalenyl]-thioxomethyl]-N-methylglycine, N-[(5-bromo-1-naphthalenyl)thioxomethyl]-N-methylglycine, N-[[6-methoxy-5-(trifluoromethylthio)-1-naphthalenyl]thioxomethyl]-N-methylglycine, and 5-hydroxy-2-[5-(trifluoromethyl)-6-methoxy-1-naphthalenyl]-3-methylthiazolium hydroxide, inner salt. The use of the therapeutically acceptable salts, with organic and inorganic basis, of the first three compounds also are included within the scope of the invention since they are biological equivalents of their corresponding free acids.

The first two aforementioned compounds, and their therapeutically acceptable salts, are disclosed as aldose reductase inhibitors for treating diabetic complications by K. Sestanj, N. A. Abraham, F. Bellini and A. Treasurywala in U.S. Pat. No. 4,439,617, filed Nov. 13, 1981. Similarly, the third compound and its therapeutically acceptable salts are disclosed with the same activity and indication by F. Bellini, K. Sestanj and L. G. Humber in U.S. Pat. No. 4,391,825 filed Nov. 13, 1981. The first three compounds also are described by K. Sestanj et al. in European Patent Application No. 82300940.2, published Sept. 8, 1982. The fourth compound, a cyclized product of the first compound, is disclosed as an aldose reductase inhibitor useful for treating diabetic complications by K. Sestanj and F. Bellini in U.S. Pat. No. 4,446,150, filed Sept. 21, 1982.

Unexpectedly, the aforementioned compounds now have been found to possess lipid lowering or hypolipidemic effects.

SUMMARY OF THE INVENTION

A method of lowering lipid levels in a mammal is disclosed. The method comprises administering to a mammal an effective hypolipidemic amount of a N-naphthoylglycine derivative selected from the group consisting of N-[[5-(trifluoromethyl)-6-methoxy-1-naphthalenyl]thioxomethyl]-N-methylglycine, N-[(5-bromo-1-naphthalenyl)thioxomethyl]-N-methylglycine, N-[[6-methoxy-5-(trifluoromethylthio)-1-naphthalenyl]thioxomethyl]-N-methylglycine, or a therapeutically acceptable salt of one of the aforementioned three compounds with organic or inorganic base; and 5-hydroxy-2-[5-(trifluoromethyl)-6-methoxy-1-naphthalenyl]-3-methylthiazolium hydroxide, inner salt.

DETAILS OF THE INVENTION

Hereinafter in the disclosure, N-[[5-(trifluoromethyl)-6-methoxy-1-naphthalenyl]thioxomethyl]-N-methylglycine is designated as "compound A", and N-[[5-bromo-1-naphthalenyl]thioxomethyl]-N-methylglycine, N-[[6-methoxy-5-(trifluoromethylthio)-1-naphthalenyl]thioxomethyl]-N-methylglycine and 5-hydroxy-2-[6-methoxy-5-(trifluoromethyl)-1-naphthalenyl]-3-methylthiazolium hydroxide, inner salt are designated as compounds B, C and D, respectively.

Compounds A, B and C are described in European patent application No. 82300940.2, supra. Compound D can be prepared by cyclizing compound A as follows: A solution of compound A (400 mg, 1.1 mmole) in acetic anhydridetriethylamine (1:1, v/v, 4 ml) was stirred at 20°-22° C. for 20 min. The reaction mixture was cooled in a refrigerator (4° C.) for 2 hr. The precipitate was collected and washed with cold diethyl ether, giving compound D: mp 166°-168° C.; NMR (DMSO-$d_6$) $\delta$ 3.50 (s, 3H), 4.00 (s, 3H), 6.40 (s, 1H), 7.80 (m, 5H).

The lipid lower effects of the N-naphthoylglycine derivatives, or their therapeutically acceptable salts with an organic or inorganic base, can be demonstrated by pharmacological tests. For example, the hypolipidemic properties of the derivatives were demonstrated as follows:

Male albino Sprague-Dawley rats (obtained from the Canadian Breeding Laboratories, St. Constant, Quebec, Canada), weighing 140-150 g, were kept under observation for two to three days. Thereafter, four separate studies were performed in which the active agents (in a 2% aqueous solution of polysorbate 80™, a surfactant) were given by gavage for seven consecutive days.

Animals were given compound A at doses of 5, 10 or 15 mg/kg/day in the first study; 15, 50 or 100 mg/kg/day in the second study; and 15, 25, 37.5 or 50 mg/kg/day in the third study; respectively. In the fourth study, compounds A, B, C and D (all four active agents) were given at a dose of 50 mg/kg/day to male albino Sprague-Dawley rats (obtained from Charles River Breeding Laboratories, Inc., Wilmington, Mass., U.S.A.), weighing 140-150 g. Clofibrate at a dose of 242 mg/kg/day was used as reference. Control animals were given vehicle only. Each group consisted of eight to ten rats. The animals had free access to food and water. On the last day of treatment, the rats were decapitated three hours after the last dose and the concentrations of cholesterol, phospholipids and triglycerides were determined in serum and liver.

The method of M. Kraml, Clin. Chem. Acta, 13, 442 (1966) was used for the determination of phospholipids, and the method of M. Kraml and L. Cosyns, Clin. Biochem., 2, 373 (1969) was used for the determination of triglycerides. Cholesterol was measured in the liver by the method of A. Zlatkis, B. Zak and A. J. Boyle, J. Lab. Med., 41, 486 (1953), as modified for the autoanalyzer (method Np-24). Total cholesterol and high density lipoprotein cholesterol (HDL-C) in the serum were determined enzymatically using the method of C. C. Allain, L. S. Poon, C. S. A. Chang, W. Richmond and P. C. Fu, Clin. Chem. 20, 470 (1974).

When tested in the preceding manner, compound A had no effect on serum lipids at oral doses of 5, 10 or 15 mg/kg/day. However, at the higher dose levels, the agent decreased serum triglycerides, and low density lipoprotein cholesterol (LDL-C), including very low density lipoprotein-cholesterol (VLDL-C), in a dose-dependent fashion (see Table I). Liver weight was unaffected (see Table II). Liver cholesterol and phospholipids were increased at doses above 15 mg/kg/day, albeit less consistently. A decrease in liver triglycerides was evident at doses of 25 and 100 mg/kg/day.

When tested in the same manner at a dose of 50 mg/kg/day (the fourth study), compounds A, B, C and D significantly lowered serum triglycerides and phospholipids. There was no effect on liver weight. Liver phospholipids were increased and compound C slightly increased liver cholesterol.

The inconsistent changes in liver lipids in the preceding studies were not considered to be pharmacologically important.

As expected, clofibrate significantly lowered serum lipids and significantly increased liver weight (see Table II). All groups showed a normal food intake, about 20 gm/rat/day, and no changes in body weight.

TABLE I

Effect of N—[[5-(Trifluoromethyl)-6-methoxy-1-naphthalenyl]thioxomethyl]-N—methylglycine (Compound A)

| Study | Group | Dose (mg/kg/day) | Body weight gain (g) | Serum lipids (mg/dl) Triglyceride glycerol | Cholesterol Total | Cholesterol HDL | Cholesterol LDL (+VLDL) | Phospholipid phosphorus |
|---|---|---|---|---|---|---|---|---|
| I | Control | — | 57.2 ± 1.93 | 8.20 ± 0.47 | 68.5 ± 3.94 | 41.9 ± 2.34 | 26.6 ± 1.83 | 4.36 ± 0.21 |
| | Clofibrate | 242 | 57.9 ± 2.06 | 5.84 ± 0.46$^{c}$ | 56.1 ± 2.45$^{b}$ | 36.7 ± 1.59 | 19.4 ± 1.20 | 3.58 ± 0.10$^{c}$ |
| | Compound | 5 | 54.0 ± 1.52 | 8.53 ± 0.93 | 70.3 ± 2.02 | 41.3 ± 1.67 | 29.0 ± 0.82 | 4.36 ± 0.87 |
| | A | 10 | 54.4 ± 1.67 | 8.62 ± 0.94 | 67.6 ± 2.20 | 41.8 ± 1.01 | 24.8 ± 1.32 | 4.11 ± 0.14 |
| | | 15 | 57.4 ± 2.69 | 9.00 ± 0.61 | 68.0 ± 3.48 | 42.6 ± 2.63 | 25.4 ± 1.15 | 4.28 ± 0.15 |
| II | Control | — | 62.7 ± 3.11 | 9.06 ± 0.92 | 74.7 ± 3.12 | 44.9 ± 1.66 | 30.0 ± 1.73 | 5.14 ± 0.24 |
| | Clofibrate | 242 | 61.4 ± 3.17 | 4.66 ± 0.43$^{d}$ | 55.8 ± 2.94$^{d}$ | 37.1 ± 1.90$^{c}$ | 18.7 ± 1.36$^{d}$ | 4.12 ± 0.16$^{c}$ |
| | Compound | 15 | 59.2 ± 1.80 | 6.14 ± 0.63$^{b}$ | 70.7 ± 2.85 | 46.5 ± 1.97 | 24.2 ± 1.51$^{b}$ | 4.63 ± 0.19 |
| | A | 50 | 56.5 ± 2.36 | 5.54 ± 0.41$^{c}$ | 63.9 ± 2.37$^{b}$ | 41.9 ± 1.24 | 22.0 ± 1.52$^{c}$ | 4.34 ± 0.10$^{c}$ |
| | | 100 | 53.4 ± 1.50 | 3.78 ± 0.41$^{d}$ | 68.0 ± 3.46 | 46.7 ± 1.81 | 21.4 ± 1.95$^{c}$ | 4.30 ± 0.18$^{b}$ |
| III | Control | — | 59.9 ± 1.73 | 12.4 ± 0.77 | 65.0 ± 2.28 | 34.8 ± 1.21 | 29.3 ± 1.53 | 4.81 ± 0.17 |
| | Clofibrate | 242 | 58.0 ± 2.54 | 4.81 ± 0.29$^{d}$ | 45.3 ± 1.26$^{d}$ | 30.2 ± 1.05$^{b}$ | 15.1 ± 1.03$^{d}$ | 3.78 ± 0.10$^{d}$ |
| | Compound | 15 | 59.7 ± 1.46 | 8.31 ± 0.73$^{c}$ | 57.3 ± 1.82$^{b}$ | 35.5 ± 1.43 | 21.8 ± 1.11$^{d}$ | 4.23 ± 0.10$^{b}$ |
| | A | 25 | 56.6 ± 1.54 | 6.57 ± 0.44$^{d}$ | 61.6 ± 1.00 | 39.1 ± 0.76$^{c}$ | 22.5 ± 1.01$^{c}$ | 4.21 ± 0.06$^{c}$ |
| | | 37.5 | 55.9 ± 2.63 | 6.61 ± 0.42$^{d}$ | 61.0 ± 2.62 | 39.6 ± 1.63$^{b}$ | 21.4 ± 1.28$^{c}$ | 4.36 ± 0.14 |
| | | 50 | 61.3 ± 3.28 | 6.48 ± 0.54$^{d}$ | 59.7 ± 1.86 | 40.3 ± 1.00$^{c}$ | 19.1 ± 1.40$^{d}$ | 4.45 ± 0.13 |

[a]Results are expressed as mean ± SEM for 8-10 rats/group.
[b]P < 0.05 (Student's t test)
[c]P < 0.01 (Student's t test)
[d]P < 0.001 (Student's t test)

TABLE II

Effect of N—[[5-(Trifluoromethyl)-6-methoxy-1-naphthalenyl]thioxomethyl]-N—methylglycine (Compound A)

| Study | Group | Dose (mg/kg/day) | Liver weight (g) | Liver lipids (mg/100 g) Cholesterol | Phospholipid phosphorus | Triglyceride glycerol |
|---|---|---|---|---|---|---|
| I | Control | — | 10.2 ± 0.27 | 230 ± 4.64 | 130 ± 1.89 | 56.5 ± 3.84 |
| | Clofibrate | 242 | 13.2 ± 0.37$^{d}$ | 195 ± 5.00$^{d}$ | 139 ± 1.86$^{c}$ | 72.2 ± 5.63$^{b}$ |
| | Compound | 5 | 10.4 ± 0.21 | 229 ± 4.38 | 139 ± 4.80 | 54.9 ± 1.61 |
| | A | 10 | 10.1 ± 0.25 | 234 ± 4.13 | 136 ± 1.98 | 58.6 ± 2.20 |
| | | 15 | 10.9 ± 0.31 | 225 ± 4.93 | 141 ± 2.41$^{c}$ | 60.1 ± 2.76 |
| II | Control | — | 11.3 ± 0.30 | 241 ± 4.43 | 114 ± 2.01 | 52.3 ± 2.78 |
| | Clofibrate | 242 | 13.5 ± 0.38$^{d}$ | 226 ± 5.56 | 148 ± 2.88$^{d}$ | 76.0 ± 8.20$^{b}$ |
| | Compound | 15 | 10.8 ± 0.30 | 258 ± 5.70$^{b}$ | 120 ± 2.67$^{c}$ | 49.1 ± 1.58 |
| | A | 50 | 10.8 ± 0.27 | 268 ± 7.53$^{c}$ | 122 ± 1.18$^{d}$ | 55.5 ± 3.03 |
| | | 100 | 10.7 ± 0.29 | 262 ± 7.62$^{b}$ | 135 ± 2.42$^{d}$ | 43.4 ± 2.18$^{b}$ |
| III | Control | — | 8.76 ± 0.17 | 254 ± 3.74 | 160 ± 2.43 | 69.0 ± 5.38 |
| | Clofibrate | 242 | 11.0 ± 0.30$^{d}$ | 220 ± 1.36$^{d}$ | 177 ± 2.12$^{d}$ | 67.4 ± 4.12 |
| | Compound | 15 | 8.52 ± 0.21 | 259 ± 3.59 | 153 ± 1.62$^{b}$ | 63.0 ± 2.65 |
| | A | 25 | 8.58 ± 0.20 | 263 ± 4.00 | 157 ± 1.63 | 52.1 ± 1.77$^{c}$ |
| | | 37.5 | 8.72 ± 0.17 | 269 ± 4.80$^{b}$ | 159 ± 2.56 | 61.6 ± 4.46 |
| | | 50 | 8.71 ± 0.28 | 269 ± 7.59 | 161 ± 2.53 | 58.7 ± 3.53 |

[a]Results are expressed as mean ± SEM for 8-10 rats/group.
[b]P < 0.05 (Student's t test)
[c]P < 0.01 (Student's t test)
[d]P < 0.001 (Student's t test)

In summary, the preceding test demonstrated that compound A produces dose-dependent decreases of serum triglycerides and LDL (+VLDL) cholesterol while having no effect on liver weight, food intake or body gain. At high doses, compound A also decreases serum phospholipids. Similarly, compounds B, C and D significantly decrease serum triglycerides and phospholipids.

As far as the applicant is aware, the finding of lipid lowering properties for compounds A, B, C and D represents a novel and unexpected property for aldose reductase inhibitors. Their analogs, described in the above noted U.S. patent applications, also exhibit to some extent a similar property.

When a N-naphthoylglycine derivative of this invention, or a therapeutically acceptable salt thereof with an organic or inorganic base, is used as a hypolipidemic agent in a mammal, e.g. man, rats or dogs, the agent is used alone or in combination with pharmacologically acceptable carriers, the proportion of which is determined by the solubility and chemical nature of the agent, chosen route of administration and standard biological practice. For example, the agent is administered orally in solid form, e.g. capsule or tablet. Also, it can be administered orally in the form of a suspension or solution, or it may be injected parenterally. For parenteral administration, the agent can be used in the form of a sterile solution containing other solutes, for example, enough saline or glucose to make the solution isotonic.

The dosage of the active agent of this invention as a hypolidemic agent will vary with the form or administration and the particular host as well as the age and condition of the host under treatment. Generally, treatment is initiated with small dosages substantially less than the optimal dose of the compound. Thereafter, the dosage is increased by small increments until the optimal effect under the circumstances is reached. In general, the active agents of this invention are most desirably administered at a concentration that will generally afford effective results without causing any harmful or deleterious side effects. The effective hypolipidemic amount of the agent, which is a multiple of the amount to treat diabetic complications for that particular agent, usually ranges from about 1.0 mg to about 200 mg per kilogram of body weight per day, although as aforementioned variations will occur. However, a dosage level that is in the range of from about 25 mg to about 100 mg per kilogram of body weight per day is employed most desirable in order to achieve effective results.

Unit dosage forms such as capsules, tablets, pills and the like may contain from about 5.0 mg to about 250 mg of the active agent. Thus, for oral administration, capsules can contain from between about 5.0 mg to about 250 mg of the active agent with or without a pharmaceutical diluent. Tablets, either effervescent or noneffervescent, can contain between about 5.0 to 250 mg of the active agent together with conventional pharmaceutical carriers. Thus, tablets which may be coated and either effervescent or noneffervescent may be prepared according to the known art. Inert diluents or carriers, for example, magnesium carbonate or lactose, can be used together with conventional disintegrating agents for example, magnesium sterate.

Syrups or elixirs suitable for oral administration can be prepared from water soluble salts, for example, sodium N-[[5-(trifluoromethyl)-6-methoxy-1-naphthalenyl]thioxomethyl]-N-methylglycinate, and may advantageously contain glycerol and ethyl alcohol as solvents or preservatives.

The active agents of this invention, or a therapeutically acceptable salt thereof, also can be used in combination with known hypolipidemic agents, for example, clofibrate, for reduction of elevated lipids in a mammal. When used in this combination, the active agent can be administered sequentially or simultaneously in combination with an effective amount of the known hypolipidemic agent. Suitable methods of administration, compositions and dosages of clofibrate is described in the ∓Physician's Desk Reference", Medical Economics Company, Oradell, N.J., 1983, pp 618–619, for example, 0.5 to 2.0 g per patient per day in divided dosages. The active agent, or a therapeutically acceptable salt thereof, in combination with a known hypolipidemic agent is used in the same manner as described herein for its use alone.

What is claimed:

1. A method for lowering lipid levels in a mammal in need thereof which comprises administering to the mammal an effective hypolipidemic amount of a N-naphthoylglycine derivative selected from the group consisting of N-[[5-(trifluoromethyl)-6-methoxy-1-naphthalenyl]thioxomethyl]-N-methylglycine, N-[(5-bromo-1-naphthalenyl)thioxomethyl]-N-methylglycine, N-[[6-methoxy-5-(trifluoromethylthio)-1-naphthalenyl]thioxomethyl]-N-methylglycine, or a therapeutically acceptable salt of one of the aforementioned three compounds with an organic or inorganic base; and 5-hydroxy-2-[5-(trifluoromethyl)-6-methoxy-1-naphthalenyl]-3-methylthiazolium hydroxide, inner salt.

2. The method of claim 1 wherein the effective amount ranges from 1.0 to 200 mg per kilogram of mammal body weight per day.

3. The method of claim 1 wherein the effective amount ranges from 25 to 100 mg per kilogram of mammal body weight per day.

4. The method of claim 3 wherein the N-napthoylglycine derivative is N-[[5-(trifluoromethyl)-6-methoxy-1-naphthalenyl]thioxomethyl]-N-methylglycine, or a therapeutically acceptable salt thereof with an organic or inorganic base.

5. The method of claim 3 wherein the N-naphthoylglycine derivative is N-[(5-bromo-1-naphthalenyl)thioxomethyl]-N-methylglycine, or a therapeutically acceptable salt thereof with an organic or inorganic base.

6. The method of claim 3 wherein the N-napthoylglycine derivative is N-[[6-methoxy-5-(trifluoromethylthio)-1-naphthalenyl]thioxomethyl]-N-methylglycine, or a therapeutically acceptable salt thereof with an organic or inorganic base.

7. The method of claim 3 wherein the N-naphthoylglycine derivative is 5-hydroxy-2-[5-(trifluoromethyl)-6-methoxy-1-naphthalenyl]-3-methylthiazolium hydroxide, inner salt.

8. A method of lowering serum triglycerides, and low density lipoprotein cholesterol in a mammal in need thereof which comprises administering to the mammal an effective hypolipidemic amount of N-[[5-(trifluoromethyl)-6-methoxy-1-naphthalenyl)]thioxomethyl]-N-methylglycine, or a therapeutically acceptable salt thereof with an organic or inorganic base.

9. The method of claim 8 wherein the effective amount ranges from 25 to 100 mg per kilogram of body weight per day.

* * * * *